(12) United States Patent
Shachar et al.

(10) Patent No.: US 8,145,434 B2
(45) Date of Patent: Mar. 27, 2012

(54) METHOD AND APPARATUS FOR FORMING A HOMEOSTATIC LOOP EMPLOYING AN APTAMER BIOSENSOR

(75) Inventors: Josh Yehoshua Shachar, Santa Monica, CA (US); Winston H. Wu, Alhambra, CA (US); Leslie Farkas, Ojai, CA (US); Thomas Chen, La Canada, CA (US)

(73) Assignee: Pharmaco-Kinesis Corporation, Inglewood, CA (US)

( * ) Notice: Subject to any disclaimer, the term of this patent is extended or adjusted under 35 U.S.C. 154(b) by 476 days.

(21) Appl. No.: 12/422,125

(22) Filed: Apr. 10, 2009

(65) Prior Publication Data

US 2010/0262375 A1  Oct. 14, 2010

(51) Int. Cl.
*G06F 11/00* (2006.01)
(52) U.S. Cl. .......................................................... 702/19
(58) Field of Classification Search .................... 702/22, 702/23, 182–185, 188; 435/7.1
See application file for complete search history.

(56) References Cited

U.S. PATENT DOCUMENTS 6,846,638 B2 * 1/2005 Shipwash ...................... 435/7.1

* cited by examiner

*Primary Examiner* — Edward Raymond
(74) *Attorney, Agent, or Firm* — Marcus C. Dawes; Daniel L. Dawes

(57) ABSTRACT

A novel architecture solid-state biosensor for label-free detection of vascular endothelial growth factor (VEGF) hybridization is presented. The new device is realized by forming a matrix array of parallel capacitors, thus allowing the realization of low-cost, portable, fully integrated devices. The detection mechanism is based on an electrochemical binding of circulating VEGF to an immobilized VEGF aptamer; whereby binding of these two compounds modulates the threshold voltage of a novel circuit, changing the impedance (capacitance) of the circuit. This novel circuit is further characterized by an electrode coded with a p-Si substrate, enhancing the affinity between the VEGF molecules and the aptamer. An apparatus forming a fluid cell is configured so as to enable the flow for delivering VEGF samples onto the active surface of the chip. The device has an array of parallel capacitors which act as an integrated, individual counter-electrode, computational apparatus which employs the sensory output over the time domain so as to enable detection, reporting and formation of a homeostatic loop for VEGF measurements. Moreover, this detector is able to provide an accurately measured and quantifiable rate of change of the VEGF molecules in-vivo, providing real time feedback of this important biomarker which may be used to measure response of the tumor to delivered chemotherapeutic agents and biological response modifiers (BRMs) for the purpose of determining tumor burden.

17 Claims, 12 Drawing Sheets

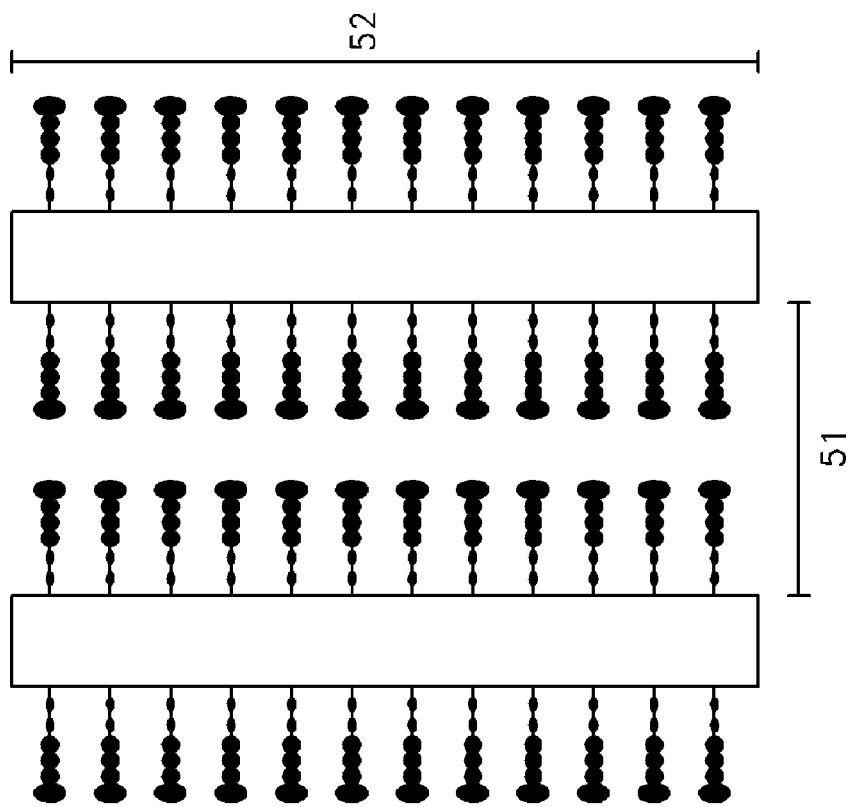

METHOD AND APPARATUS FOR FORMING A HOMEOSTATIC LOOP EMPLOYING AN APTAMER BIOSENSOR

FIELD OF THE DISCLOSURE

The present invention is directed to chemical Biosensors. More particularly, the present invention is directed to fixed parallel plate chemical biosensors and capacitor arrays and methods of making same.

BACKGROUND

Vascular endothelial growth factor (VEGF) plays a critical role during normal angiogenesis and also in the pathological angiogenesis that occurs in a number of diseases, including cancer. Initial attempts to block VEGF by using the humanized monoclonal antibody bevacizumab (Avastin, Genentech/Roche), and two kinase inhibitors sorafenib (Nexavar; Bayer) and sunitinib (Sutent, Pfizer) targeting the VEGF receptor (VEGFR) tyrosine kinases are beginning to show promise in human cancer patients, underscoring the importance of optimizing VEGF blockade. The growth of human tumors and development of metastases depend on the de novo formation of blood vessels to reach and provide nutrients for the hypoxic tumor microenvironment. The formation of new blood vessels is tightly regulated by specific growth factors that target receptor tyrosine kinases (RTKs).

VEGF and the Flk-1/KDR RTK have been implicated as the key endothelial cell-specific factor signaling pathway required for pathological angiogenesis, including tumor neovascularization. Inhibition of the VEGF tyrosine kinase signaling pathway blocks new blood vessel formation in growing tumors, leading to stasis or regression of tumor growth. Advances in understanding the biology of angiogenesis have led to the development of several therapeutic modalities for the inhibition of the VEGF tyrosine kinase signaling pathway. A number of these modalities are under investigation in clinical studies to evaluate their potential to treat various forms of human cancer, but the ability of such studies are limited by the fact that local, real time in vivo measurement of the VEGF level and the trends of the VEGF transduction is not readily available.

In normal development VEGF is a crucial regulator of vascular development during embryogenesis (vasculogenesis) and blood-vessel formation in the adult (angiogenesis). In tumor progression, activation of VEGF pathways promotes tumor vascularization, facilitating tumor growth and metastasis. Abnormal VEGF function is also associated with other diseases including atherosclerosis, psoriasis, age related macular degeneration, diabetic blindness, rheumatoid arthritis, and hyperthyroidism. The members of the VEGF and VEGF-receptor protein families have distinct but overlapping ligand-receptor specificities, cell-type expression, and function. VEGF-receptor activation in turn regulates a network of signaling processes in the body that promote endothelial cell growth, migration, and survival.

Biosensors which continuously monitor their surroundings to provide background statistics and warnings against unhealthy conditions are known to be used in medical technology. The following is a brief overview of the prior art including a discussion of some prior art biosensors. Details of the literature are cited by the references noted in the body of this application. There are numerous examples of, for example, gravimetric biosensors. The basis of detection is the decrease in the resonant frequency of a resonator that occurs as analyte species attach to the resonating element. Analyte specificity is conferred for biological analytes by functionalizing (treating) the exposed surface of the resonator with ligands that recognize and bind to the target analyte species. Examples of suitable binding entities for target biological analytes include antibodies, receptors, lectins, aptamers and oligonucleotides.

In one gravimetric biosensor, the immobilized binding group is located in one or more areas on the surface of the membrane whose locations on the membrane, sizes and area immobilization densities are designed to maximize the observed frequency and/or amplitude shifts on target analyte binding and to maximize the discrimination between all combinations of specific and non-specific binding. This discrimination may take three forms: (a) change in resonant frequency of the membrane, (b) appearance or disappearance of higher order harmonic vibrations, or (c) change in amplitude decay rates. In such a biosensor, a single membrane may be comprised of a plurality of individually addressable elements for actuation and for sensing purposes. This technique permits the specific excitement of selected higher order vibrational modes and enables simultaneous vibration actuation of an alarm circuit or like devices. The principles of acoustic wave, sometimes referred to as gravimetric sensors, are well known and applications have appeared in the literature for more than a decade.

Molecular interactions can be detected electronically through the polarizability of biological macromolecules, optically through the use of fluorescencing tags, radiometrically through the use of radioactive labeled tags, or acoustically. Recently, MEMS based sensors have been incorporated in the biotechnical and biomedical fields. Application of acoustic biosensors, range from cell detection, glucose biosensing, antibody-antigen recognition, and protein adsorption.

Piezoelectric quartz crystal microbalances (QCMs) have been used since the late 1950s to detect gas and liquid phase analytes. Application of QCM technology to biological analytes is more recent. QCMs have been used to track the non-specific adsorption of proteins to unmodified and modified quartz crystal surface electrodes. Immobilization of antibodies to the crystal surface confers analyte specificity.

Since the prior art is extensive we have elected to cite some fundamental innovations of the art of biosensors, as it provides for the principles under which most of the advance applications are based on, an example is sampled by Arwin, et al. U.S. Pat. No. 4,072,576 teaches a method for studying biochemical reactions in which a substance, whose activity or concentration is to be determined, affects a substrate specific for the biochemical reaction which includes providing electrodes coated with the substrate, determining as the control value, the capacitance in a measuring device containing the electrodes, introducing the substance into the measuring device, measuring the change in capacitance, and thereby obtaining a quantitative measure of the activity or concentration of the substance present in the sample and affecting the specific substrate on the electrodes.

Schenck U.S. Pat. No. 4,238,757 describes a field effect transistor including conventional source and drain electrodes employs, in the gate region, a layer of antibody specific to a particular antigen. An electrolyte solution such as 0.155 Normal sodium chloride atop the antibody layer provides a predetermined drain current versus drain voltage characteristic for the device. Replacement of the electrolyte solution with another electrolyte solution containing the antigen alters the charge of the protein surface layer due to the antigen-antibody reaction, thus affecting charge concentration in a semiconductor inversion layer in the transistor. The time rate of change of drain current thus provides a measure of the antigenic protein concentration in the replacement solution.

Rice U.S. Pat. No. 4,314,821 describes a method and kit for determining the total amount of an immunologically-reactive substance in a liquid sample containing interfering material capable of binding to an antigen. The method involves the steps of contacting a liquid sample containing or suspected of containing an antibody with the surface of a piezoelectric oscillator having a layer of antigen specific for the antibody attached thereto; washing and drying the oscillator; measuring the resonance frequency of the oscillator; contacting said surface of the oscillator with a liquid reagent containing an excess amount of a substance specifically reactive with all of the antibody bound to the oscillator. Further, washing and drying the oscillator; and measuring the change in resonance frequency of the oscillator form the first measurement whereby the amount of total antibody bound to the oscillator is distinguished from the interfering material bound in earlier step.

Malmros U.S. Pat. No. 4,444,892 introduces a sensor and semiconductor device for determining the concentration of an analyte in a medium. The device features an element constructed of semi conductive organic polymer associated with a binding substance having specific affinity for the analyte.

Iida, et al. U.S. Pat. No. 4,900,423 teaches of technique where an enzyme sensor comprising enzyme acting specifically on a substrate and a transducer for converting the quantitative change of a substance or heat which is produced or consumed during an enzyme reaction to an electrical signal, wherein the enzyme is glucokinase is disclosed. Iida teaches that a determination of an amount of glucose in a sample is possible as well as an accurate determination of adenosine-5'-triphosphate (ATP). A response time of the sensor is almost constant after a long-term use and a decrease of the detecting ratio is very small.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole. Additional objects and advantages of the current invention will become apparent to one of ordinary skill in the art upon reading the specification.

The present disclosure describes an apparatus that allows an architecture for constructing a solid-state biosensor for label-free detection of VEGF hybridization. In an embodiment, the device is realized by forming a matrix array of parallel capacitors, so as to achieve a high ratio signal to the lowest minimal electrochemical variations, accompanied by an electrical equivalent value, thus allowing the realization of low-cost, portable, fully integrated devices.

The present disclosure is directed to the formation of biosensors and, more particularly, to a capacitive array of an integrated platform of the type that are fabricated using solid state fabrication techniques in conjunction with an oligonucleotide element known as aptamers,—(oligonucleotide ligands that are selected for high-affinity binding to molecular targets),—which form the dielectric and the hybridization surface of the capacitor plates. The proposed invention aims to emulate the growth rate of tumor development as a function of its VEGF level in the sensor chamber while measuring the binding rate of VEGF molecules to the capacitor plate, vector/trends of tumor' binding rate of VEGF molecules is simulated by the equivalent circuit of the apparatus. The bio-capacitor calculates the state of the system so as to, further act as a level-switch detector for the VEGF concentration within the proposed chamber.

As discussed above, VEGF plays a critical role during normal angiogenesis and also in the pathological angiogenesis that occurs in a number of diseases, including cancer. Initial attempts to block VEGF by using the humanized monoclonal antibody bevacizumab (Avastin, Genentech/Roche), and two kinase inhibitors sorafenib (Nexavar; Bayer) and sunitinib (Sutent, Pfizer) targeting the VEGF receptor (VEGFR) tyrosine kinases are beginning to show promise in human cancer patients, underscoring the importance of optimizing VEGF blockade. Therefore, an implanted in-vivo device that accurately provides real time feedback on VEGF levels and thereby is able to logically regulate, attenuate or modify the intake of anti-angiogenic agents is crucial for any finely tuned anti-angiogenesis therapy. The presently described system measures VEGF levels by emulating the process whereby VEGF binds to an immobilized VEGF aptamer within a known time domain, providing an appropriate feedback based on the VEGF level in the regulated loop.

The interactions between VEGF protein and their receptors are annotated by the respective binding of the aptamer and the VEGF receptor within the controlled conditions in the apparatus chamber. Details of signaling events and their biological outcome are concisely illustrated by simulating the binding rate of the VEGF molecule-binding to the aptamer present in the proposed apparatus' chamber; hence, such parallel process provides the necessary quantitative trends and concentration values in the equivalent circuit of the proposed apparatus.

Fabrication of the proposed VEGF detector is presented, using the significant improvements made in techniques and equipment for fabricating miniature devices and, consequently, the use of micro machined equipment is outlined. Improvements in silicon manufacturing and high-precision machinery opened the area now known as Micro-ElectroMechanical Systems (MEMS) for research and development of applications. Subsequent development of microscale valves, pumps, channels and heat exchangers allowed for manipulation of extremely small fluid volumes. Coupled with mass fabrication techniques refined in the integrated circuit (IC) and MEMS communities, microfluidics and microchemical systems are employed in realizing the proposed invention.

In the present application, microscale solutions can be used to minimize cost and impact and prolong lifetime due to limited use of consumables and the inherent need to monitor the process of the tumor growth and elimination for duration exceeding a one-time use. The proposed invention offers an advanced configuration, which includes a coordinated and flexible sensor system with multiple devices operating on a single fluid sample to carry out fully automated chemical analysis with the aid of on-board processing logic.

As discussed above, biosensors for detecting the presence of molecules of interest have application in numerous fields, including medical diagnosis, biomedical research, and detection of agents used in biological and chemical warfare. The need exists for an inexpensive, compact sensor with high sensitivity for detecting VEGF molecules in a Real Time, In-Vivo, Label Free environment, so as to report on the conditions such as Trends and Concentrations, further enabling the formation of a closed feedback loop to effectively regulate, (attenuate, modify), the biological activity using medications such as noted by this application. Such an apparatus is disclosed in the present disclosure.

The apparatus can detect the presence of the VEGF molecules by the use of mechanism based on an electrochemical binding of an aptamer suitable to bind to VEGF molecule.

In an embodiment, the sensor has an electrical polarity so as to naturally attract the intrinsically negative electric charge of VEGF molecules, while further modulating the threshold voltage of the circuit. In an embodiment, the electrical polarity can be modulated so as to attract and then release the VEGF molecules to prevent a buildup of VEGF molecules on the sensor and to keep a continuous flow of biological fluids flowing through the sensor.

The sensor is constructed with an electrode preferably coded with a p-Si substrate so as to enhance the affinity between the VEGF molecules and the aptamer which changes the impedance (capacitance) of the circuit.

The need for such a sensor is further augmented by the use of a fluid-cell configured so as to enable the flow of VEGF samples on the active surface of the chip.

The device can have an array of parallel capacitors which act as integrated, individual counter-electrode. The device can also be equipped with a computational apparatus so as to render the sensory output over the time domain, resulting in detection, reporting and formation of a homeostatic loop.

The device output is preferably configured as part of an active delivery mechanism for measurements as well as possible therapeutic intervention of a medicating agent(s).

The device can provide an accurate measured and quantifiable rate of change of the VEGF molecules in-vivo, and enables improved diagnosis of tumor markers As a results of such information (VEGF level and vectorial trends), the device with its auxiliary circuit improves the delivery system of chemotherapeutic agents and biological response modifiers (BRMs) for the purpose of tumor burden reduction and elimination.

In an embodiment, a simple and robust, as well as mild and reversible method is provided which can reliably detect in one operation a VEGF molecule and/or create an associated arrangement for carrying out the method.

An object may be achieved according to at least one embodiment of the invention by a binding of the specified aptamer sequence of method steps.

An associated arrangement may be included for carrying out the method of at least one embodiment.

In at least one embodiment, measurement is carried out in each case after the VEGF aptamer is bound to circulating VEGF, and its electrical value is counted in the time domain, stored, and reported.

In a specific further development, the method of at least one embodiment advantageously makes use of the methodology of electrochemical detection, especially of redox cycling in combination with an aptamer, label. The aptamer capture molecules are located on a solid support material, preferably a silicon chip with insulated electrodes.

At least one device for monitoring and controlling the hybridization of the VEGF molecules over the matrix array positions of the chip, and one device for controlling the rate of liquid flow and associated detection device are present on the arrangement of at least one embodiment. For this purpose, the sensor chip can be connected to a microfluidics system including precision pump in at least one embodiment. An example of a microfluidics system is described in U.S. patent application Ser. No. 12/143,720, entitled Magnetic Breather Pump and Method for Treating a Brain Tumor Using the Same, filed Jun. 20, 2008, the entirety of which is incorporated herein by reference.

Various embodiments relate to signal amplification methods for multiple biological assays.

In general, biological target complexes are tagged by a seed substance that can catalyze the formation of a surface-enhanced substrate such as aptamer. The target complexes can then bind to capture reagents which include a VEGF label. The substrate is then generated on the seed substance through reduction of immobilized VEGF aptamer (Macugen). The target signals are detected by Pegaptanib, (an aptamer, a pegylated modified oligonucleotide, which adopts a three-dimensional conformation that enables it to bind to extracellular VEGF. (Under in vitro testing conditions, pegaptanib binds to the major pathological $VEGF_{165}$ isoform).

Accordingly, in one embodiment, a biological target complex including a target analyte associated with a first specific binding member is provided. The target complex further includes a second specific binding member that binds to the first specific binding member forming a target complex. The second specific binding member includes a seed particle suitable for catalyzing the formation of a surface enhanced aptamer VEGF substrate. Subsequently, the complex substrate can be activated by means of the electronic circuit to provide the necessary change in impedance effect. These and other important objects will be apparent from the descriptions of the instant invention which follow.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and together with the detailed description of the invention, serve to explain the principles of the present invention.

FIG. 2A is a top view of an orthographic representation of the capacitive VEGF sensor.

DETAILED DESCRIPTION

Figure 1:
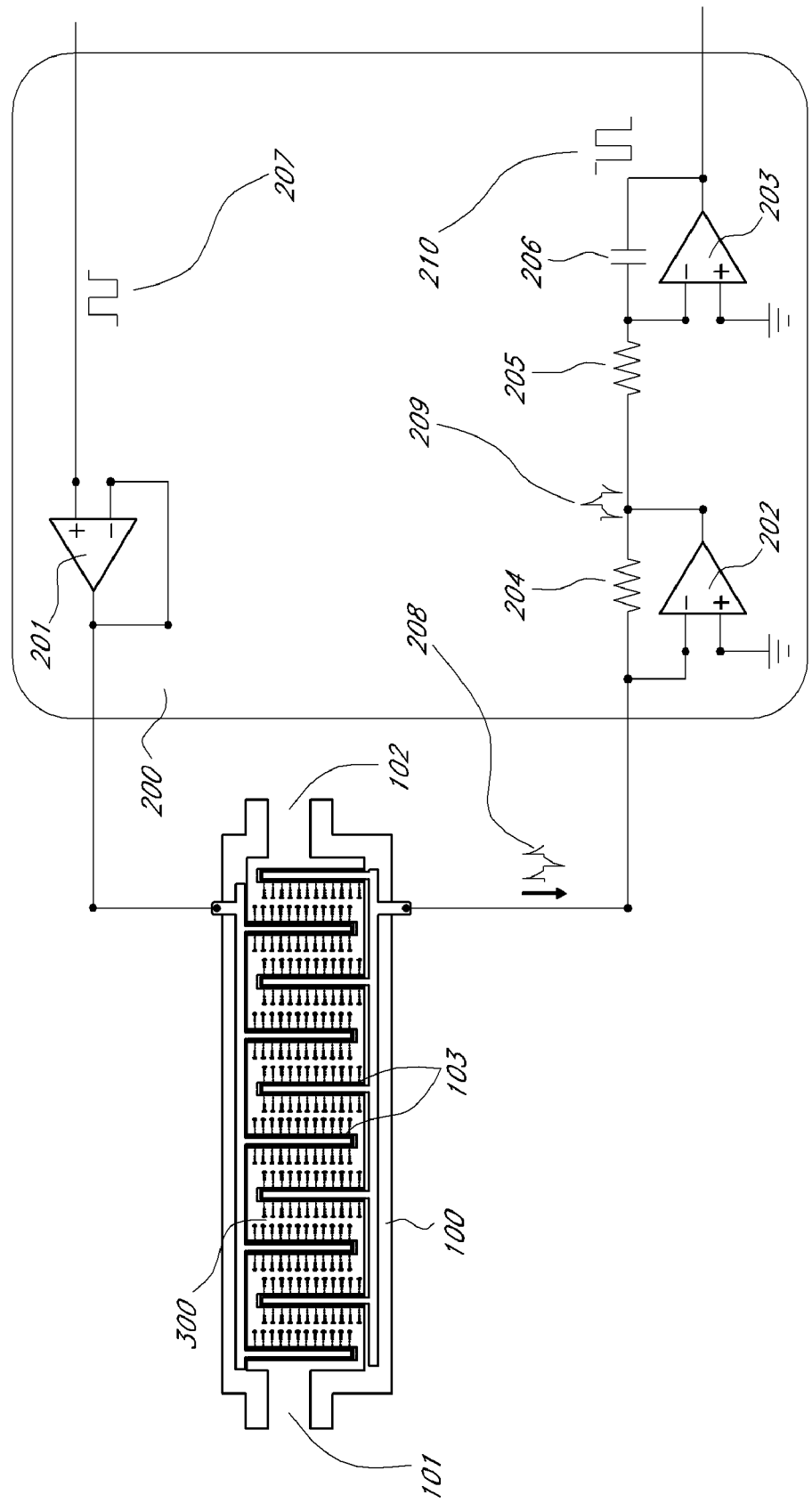
FIG. 1 is an orthographic cross section of the apparatus with a schematic representation of the electronic detection module.

Unless defined otherwise, all technical and scientific terms used herein have the same meanings as commonly understood by one of ordinary skill in the art to which this invention belongs. Although any methods and materials similar or equivalent to those described herein can be used in the practice or testing of the subject matter of the present disclosure, the methods, devices, and materials are now described. All publications mentioned herein are incorporated herein by reference for the purpose of describing and disclosing the materials and methodologies which are reported in the publications which might be used in connection with the disclosure. Nothing herein is to be construed as an admission that the invention is not entitled to antedate such disclosure by virtue of prior invention.

"VEGF and anti-VEGF aptamer hybridization" as used herein refer to the process of hybridization of VEGF 1, to the anti-VEGF aptamer 11, and is accomplished via the molecular recognition between VEGF and the aptamer. The aptamer binds specifically to the $VEGF_{165}$ isoform at its heparin-binding domain (HBD) instead of the more well-known receptor-binding domain, with most of the binding energy (3 kcal/mole or 23% of total) contributed by HBD. The heparin-binding domain of VEGF has no significant sequence or structural similarity to any known proteins and thus represents a novel heparin-binding domain. Most of the positively charged amino acid side chains are localized on one side of the carboxy-terminal sub domain or on an adjacent disordered loop in the amino-terminal sub domain. The observed distribution of surface charges suggests that these residues constitute a heparin interaction site. HBD is also the primary determinant for the affinity and specificity in the $VEGF_{165}$-aptamer complex not in vitro but also effective in vivo.

"Surface modification" as used herein refer to the process detailed by Y. Han et al., 2005 which describes preparing the $SiO_2$ surface 14, as it is cleaned with MeOH/HCl (1/1) for 30 min at room temperature, rinsed with ultra pure water (Milli-Q Gradient A10 18.2 MΩ), and dried with Argon. In the next step, the surface is modified with $NH_2$ groups by a silanization step with 3-aminopropyltriethoxysilane (APTES) either in the gas phase. For gas-phase silanization, the chips are placed in a desiccator containing a few drops of silane. The desiccator is sealed and heated above 100° C., and the chips were left to react for 1-2 h under a low pressure (~1 mbar) with the silane vapor. This technique employs biocompatible scaffolds to provide viable alternatives forming the prosthetic materials for adhesion. The use of self assembled peptide amphiphile nanofiber coated scaffold to grow the linker 12, is advantageous because of its high surface area, which permits a large number of sites for the succinic anhydride 12, adhesion and growth. (Succinic anhydride, also called dihydro-2,5-furandione, is an organic compound with the molecular formula $C_4H_4O_3$.) The fibrous nature of the coating allows the linker 12, to penetrate the surface by diffusion, and the matrices have sufficient surface area and exposure to the linker 12. The linker 12, is further combined with an amino-silanization 13. (The surface of a quartz or glass wafer ($SiO_2$ 14) is treated with different aminosilanes in solution where surface density increased sharply with the reaction time and produced the multilayer.) The amino-silanization 13, scaffolds provide viable alternatives forming the prosthetic materials for adhesion to the $SiO_2$ insulator surface 14.

"Aptamer immobilization" as used herein refers to the process detailed by H. S. Lee et al., which describes immobilization, whereby an Anti-VEGF RNA aptamer, Macugen, (650 μg/vial; 3 vials) is dissolved in phosphate buffer (PB, 200 mM, pH 8) to prepare aptamer solution at a concentration of 20 mM. Each vial is incubated at room temperature for 4 hours. After that, aptamer solution (500 μL) is added and incubated at pH 7.5 and room temperature. The resulting substrates are washed with phosphate buffer saline (PBS) and water in a sequential manner. Finally, the substrates are air-dried and the immobilization is analyzed by atomic force microscopy (AFM), indicating an average of ~3 nm increase of surface thickness due to the immobilization of anti-VEGF aptamers.

The concept of using single-stranded nucleic acids (aptamers) as affinity molecules for protein binding was initially described in 1990 (Ellington and Szostak 1990, 1992; Tuerk and Gold 1990), and is based on the ability of short sequences to fold, in the presence of a target, into unique, three-dimensional structures that bind the target with high affinity and specificity. E. W. M Ng et al., 2006, describes that aptamers are oligonucleotide ligands that are selected for high-affinity binding to molecular targets. For example, Pegaptanib sodium (Macugen; Eyetech Pharmaceuticals/Pfizer) is an RNA aptamer directed against vascular endothelial growth factor (VEGF)-165, the VEGF isoform primarily responsible for pathological ocular neovascularization and vascular permeability. Pegaptanib sodium, which is a covalent conjugate of an oligonucleotide of twenty-eight nucleotides in length that terminates in a pentylamino linker, to which two 20-kilodalton monomethoxy polyethylene glycol (PEG) units are covalently attached via the two amino groups on a lysine residue, is used due to its binding affinity to a VEGF molecules 1. The immobilized aptamer complex is used to detect circulating $VEGF_{165}$ isoform 1.

"Fabrication of silicon insulator surface" as used herein refer to the process detailed by H S Lee et al., 2008 which describes a layer of Au (100 μm) deposited to form the interleaved array of electrodes 103, inside an insulating enclosure 17. Silicon crystal for p-doping 15 is grown on the Au conductor surface 16, with a constant flow of $SiH_4$ precursor at 530° C. under the gas pressure of 50 Torr. During this process, silicon crystals are in situ doped with $B_2H_6$ as p-dopants at the relative pressure ratio of $SiH_4:B_2H_6$ to be $10:1\times10^{-3}$. The flow of $SiH_4$ is continued but $B_2H_6$ is stopped when the p-substrate 15, reaches 1 μm. After the additional Si layer reaches 10 nm, the flow of $SiH_4$ is stopped; the temperature is raised to 820° C. and gas chamber is opened to the atmospheric pressure, allowing oxidation in the dry atmosphere to form the $SiO_2$ insulation layer 14.

"Capture reagent" as used herein, is a molecule or compound capable of binding the target analyte or target reagent, which can be directly or indirectly attached to a substantially solid material. The capture agent can be any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Target analyte" as used herein, is the substance to be detected in the test sample using the present invention. The analyte can be any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof. The target analyte can include a protein, a peptide, an amino acid, a carbohydrate, a hormone, asteroid, a vitamin, a drug including those administered for therapeutic purposes as well as those administered for illicit purposes, a bacterium, a virus, and metabolites of or antibodies to any of the above substances "Target analyte-analog" as used herein, refers to a substance which cross reacts with an analyte capture reagent although it may do so to a greater or lesser extent than does the target analyte itself. The target analyte-analog can include a modified target analyte as well as a fragmented or synthetic portion of the target analyte molecule so long as the target analyte analog has at least one epitomic site in common with the target analyte of interest.

"Test sample" as used herein, means the electrolyte solution containing the target analyte to be detected and assayed using the present invention. The test sample can contain other components besides the target analyte, can have the physical attributes of a liquid, or a gas, and can be of any size or volume, including for example, a moving stream of liquid. The test sample can contain any substances other than the target analyte as long as the other substances do not interfere with the binding of the target analyte with the capture reagent or the specific binding of the first binding member to the second binding member. Examples of test samples include, but are not limited to: Serum, plasma, sputum, seminal fluid, urine, other body fluids, and environmental samples such as ground water or waste water, soil extracts, air and pesticide residues.

"Methods and reagents" used by authors for the purpose of analysis and testing of the proposed apparatus are based on information provided by H S Lee et al., 2008 paper. The following reagents were used without further purification for the propose of identifying the method: 3-Aminopropyl diethoxysilane (APDES), succinic anhydride (SA), sodium carbonate (SC), phosphate buffered saline (PBS) tablet, sodium dodecylsulfate (SDS), 1-ethyl-3-[3-(dimethylamino) propyl]carbodiimide (EDC), N-hydroxysulfo succinimide (sulfo-NHS), sodium hydroxide (NaOH), sodium chloride (NaCl) (Sigma-Aldrich Co. St. Louis, Mo.). As a detecting protein, human $VEGF_{165}$ was purchased from Cell Signaling Technology, Inc. (Danvers, Mass.). The human $VEGF_{165}$ coding cDNA is reported to be sub cloned into an expression vector and expressed in yeast. The recombinant human $VEGF_{165}$ homodimer is reported as further purified and stored in phosphate buffered saline (PBS, pH 7.4) containing 0.1% BSA. Surface plasmon resonance (SPR) was carried out using a BIAcore 2000 instrument. Atomic force microscopy (AFM) images were taken using a digital AFM instrument with Nanoscope W software. Nanometer pattern generation system (NPGS) combined with Tescan Scanning electron microscope (SEM) was used for e-beam lithography.

"Synthesis of anti-VEGF aptamer" is used by this invention to mean that an aptamer is isolated from combinatorial libraries of synthetic nucleic acids using in vitro selection methods (SELEX, Systematic Evolution of Ligands by Exponential Enrichment).

The "SELEX" process means a technique for screening a very large library of oligonucleotides with random sequences by iterative cycles of selection and amplification. As detailed in H. S Lee et al., 2008, anti-VEGF RNA aptamer with an amine terminal group is synthesized using solid-phase phosphoramidite chemistry with an oligonucleotide. The sequence of synthesized aptamers is 5'-$NH_2$-AmUmGm-CmAmGmUmUmUmGmAmGmAmAmGmUmCmGm-CmGmCmAmU-3'.

"Binding affinity of synthesized anti-VEGF RNA aptamers", means the use of surface plasmon resonance (SPR) analyses (Kang et al., 2008) for analyzing interactions between two biomolecules.

"Anti-VEGF RNA aptamers" is used by this invention to mean an Anti-VEGF RNA aptamers is dissolved in phosphate buffer salines at concentrations from ca. 30 nM to 500 nM, and then are injected over the immobilized VEGF on the sensor chips. The adsorption of aptamers onto the VEGF results in the formation of aptamer-VEGF complexes.

"Effective sensor geometry" is used by this invention to mean the physical geometry $G_x$ of the biosensor and the arrangement of its sensing structures that maximize the sensing area with minimum volume. In addition, the cross sectional area of the flow through the sensor must be larger than the cross sectional area of the flow inlet and outlet so that the physical geometry of the sensor does not impede the flow characteristics of the entire system. The capacitance due to the sensor geometry $G_{eometry}$ is described in Equation 1 using the dielectric ($\in_r$) as a variable that correlates with target analyte concentration in the test sample.

$$C_{geometry} = \varepsilon_r \varepsilon_0 \frac{A}{d} \quad (1)$$

where $\in_r$ is the combined relative permittivity (dielectric constant) of the medium consisting of VEGF molecules (after hybridization), bodily fluid, anti-VEGF aptamers, Succinic anhydride linker, Amino hybridization substance, $SiO_2$ insulator, and p-Si substrate; $\in_0$ is the permittivity of the free space (8.854×10$^{-12}$ F/m); A is the total area of electrode plates with width 52, and length 53; and d is the separation between the plates 51. The values of A and d are chosen so that the change in capacitance can be effectively measured with the following technique but the circulation flow of the body fluid through the sensor unit 100, is unrestricted. Due to the fact that the thickness of the surface when VEGF binds is about 200 nm, the separation can be as small as a few micrometers without the risk of restricting the flow due to VEGF hybridization. However, because the cross sectional area formed by $d_{cap}$ 51, and $W_{cap}$ 52, must be at least as large as the cross sectional area of flow inlet and outlet, so that it fluid flow through the sensor does not restrict the overall flow characteristics.

For example, given a 3 French inlet diameter, the minimum cross sectional area ($d_{cap} \times W_{cap}$) of fluid flow through the biosensor is approximately 100 mm×8000 mm, respectively, from microfluidics perspective. The only variable in Equation 1 is the combined dielectric constant $\in_r$ that changes with VEGF molecule hybridization with the surface. In order to maximize the effective sensing area in a small volume, the electrode plates 103, are arranged in an interdigitated fingers pattern. Following the insulator fabrication process described above, the combined thickness of one sensor plate is 102.02 μm (the sum of the thicknesses of electrode, two layers of p-substrate, two layers of insulator). With d (the distance between the plates 51) as 100 μm, the total space required for each electrode pair is 202.02 μm. Because the plate area of 1 cm² provides sufficient capacitance of around 10 μF, A is chosen as 1 cm² and $W_{cap}$ (the width of the plates 52) is chosen as 0.8 cm (see effect sensor geometry in definitions), which leads to the total length of the plates to be 1.25 cm or 12500 μm. With $L_{cap}$ (the length of the plates 53) chosen as 625 μm, there are 20 turns or electrode pairs arranged in interdigitated finger pattern. Thus, the total internal volume of the sensor is 8000 μm (D)×725 μm (H)×4040.4 μm (L).

The "Measurement technique" of the electrochemical cell, as noted by FIGS. 1, 1A, 2, & 2A, is based on the sensing principle of a variable capacitor cell where the dielectric ($\in_r$) of the electrode/solution interface model 110, is the variable. In this model, the VEGF protein 1, stranded on an anti-VEGF aptamer 11, introduces additional insulating layers 14, between electrode and solution, resulting in a measurable change in capacitive component of the interface model. The charge-based capacitance measurement (CBCM) technique can measure this change in capacitive component of the electrode-solution interface impedance. The measurement principle of this CBCM technique is to charge and discharge the VEGF electrochemical cell at an appropriate frequency, and measure its equivalent capacitance from the average current in half-period, noted in Equation 2.

$$I_{avg} = \frac{\Delta Q}{T/2} = \frac{C\Delta V}{T/2} = 2C\Delta Vf \quad (2)$$

Where $\Delta V$ and f are known and $I_{avg}$ can be measured. This measurement technique is illustrated in 200, which consists of two separate circuits. The Op Amp voltage follower 201 increases the input impedance of the electrochemical cell so that the cell can be driven by a near perfect square wave 207, from a digital output signal line from a microcontroller 401. The frequency (f) of the square wave is chosen as the maximum frequency that completely charges and discharges the capacitor in the electrochemical cell in the half period. The charging of the capacitor creates a charge field which allows the binding of the desired molecule and the discharging of the capacitor frees the molecules. This allows the device to bind and unbind so that there is not a permanent build up or binding of proteins. The second part of 200, converts $I_{avg}$ 208, into voltage value with a known resistor value $R_1$ 204, and amplified with an Op-Amp 202. $V_1$ 209, at the output of the Op Amp 202, can be calculated as shown in Equation 3.

$$V_1 = -C_{cell}R_1 \frac{dV_{in}}{dt} \quad (3)$$

An Op Amp integration circuit 203 converts the transient voltage values 209, into a square wave 210, as shown in Equation 4.

$$V_{out} = -\frac{1}{C_2}\int \frac{V_1}{R_2} dt \quad (4)$$

Substituting Equation 2 into 3, the output of 200, as a function of its input can be calculated as shown in Equation 5 leading to Equation 6.

$$V_{out} = -\frac{1}{C_2 R_2}\int -C_{cell}R_1 \frac{dV_{in}}{dt} dt \quad (5)$$

$$V_{out} = \frac{C_{cell}R_1}{C_2 R_2} V_{in} \quad (6)$$

The output voltage of 200, which is sampled by an ADC 402, is proportional to the value of $C_{cell}$.

"Homeostatic control mechanisms" is used by this invention to mean that the biosensor's measured-variables 11, are being regulated. The three components of Homeostatic control mechanisms employed are explained below. The receptor is the biosensor 100, combined with the capacitance detector circuit 200, which monitors and produces an output signal proportional to hybridized target analyte molecules (e.g., VEGF 1). The receptor senses the arrival of target analyte and sends information to a control circuit, which sets the range at which a variable is maintained. The control circuit, which is a microcontroller 401, determines an appropriate response to the stimulus. The control circuit then sends signals to an effector, which is a pump 405, to inject biological agents into the system. The homeostatic approach is used to achieve a stable state of equilibrium that limits the tumor growth while not endangering the surrounding tissues near the tumor site. If a change away from the equilibrium occurs, the control mechanism corrects the deviation by either enhancing it with positive feedback or depressing it with negative feedback.

FIG. 1 is an orthographic cross section of the biosensor apparatus with a schematic representation of the electronic detection module. The apparatus with its insulating enclosure 100, in an embodiment, is configured with fluid flow inlet 101, and a flow outlet 102. The electrolyte solution 3, flows into the biosensor via the inlet 101, and outlet 102, and possibly connected to a pump and valve arrangements as described in FIG. 5. The apparatus 100 consists of an array of electrodes coded with capture reagents which form the capacitive plates 103. The electrodes are designed in an interdigitated fingers pattern in order to maximize the sensor surface area in a small volume. The apparatus 100 is interfaced with the electronic module 200, which form the capacitance detector circuit. The detector circuit 200, includes an Operational Amplifier buffer 201; a current-to-voltage amplifier 202, involving a resistor 204; an Op Amp integration circuit 203, involving a resistor 205, and a capacitor 206. The values of the resistor 205, and capacitor 206, are matched approximately to the resistor 204, and capacitance of 100, respectively, so that the output signal 210, is approximately the same as input square wave 207. The half period of the input square wave 207, should be significantly larger than the RC constant formed by the resistor 204, and capacitance 100, so that the Op Amp 202 has enough time to discharge the sharp transitions caused by the square wave 207. As the capacitance of 100 increases with arrival of target analytes, the amplitude of output signal 210, increases proportionally. The detail mechanism behind this measurement technique is elaborated further in the definitions section above.

Figure 1A:
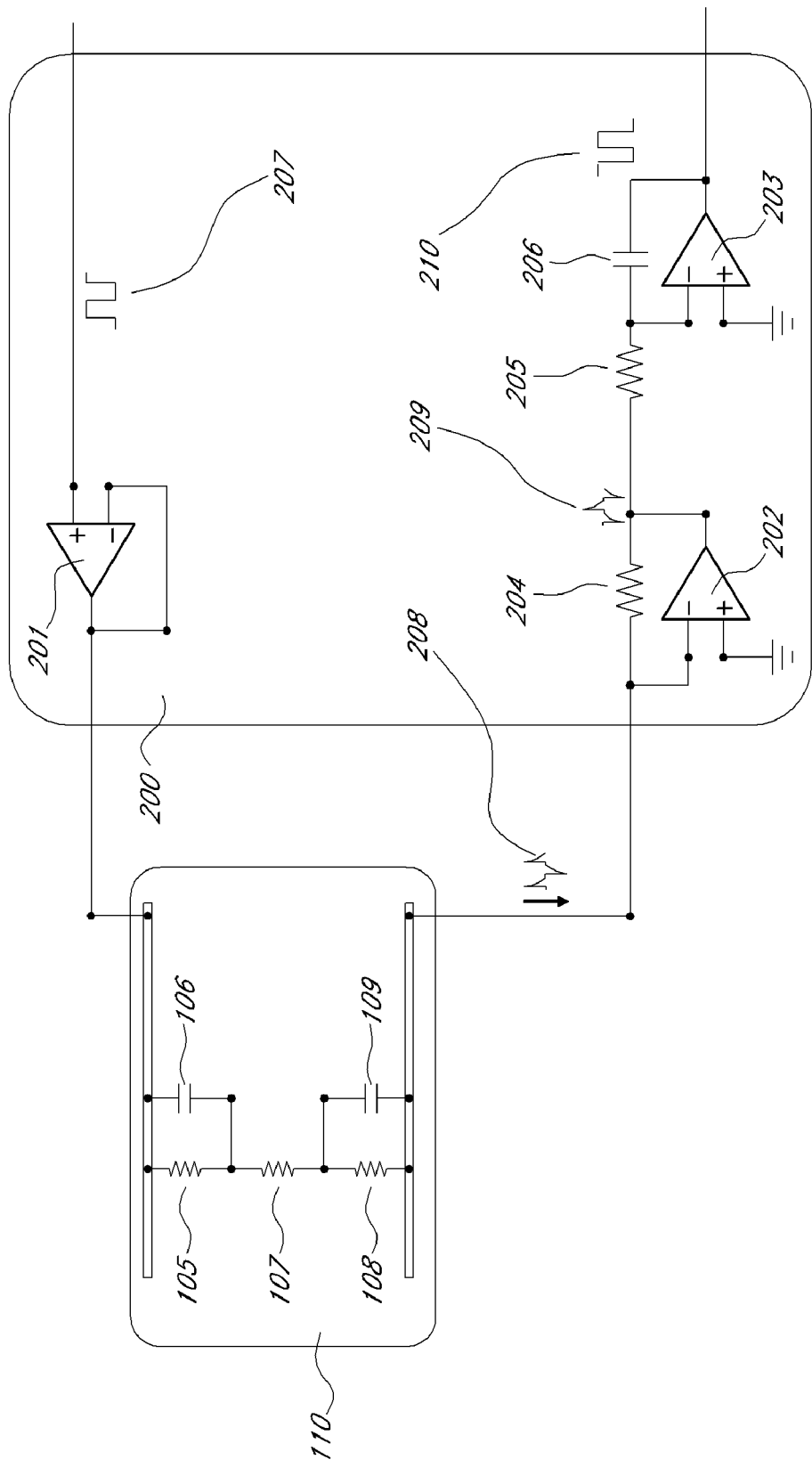
FIG. 1A is a schematic representation of the preferred embodiment of the invention depicting one cell of an equivalent electrode-electrolyte node from the capacitor array.

FIG. 1A is a schematic representation of an embodiment depicting an equivalent electrical circuit of the capacitor array 103. The circuit schematic, sectional view noted by reference designator 110, is represented as including the resistance of the interface between electrode A and test sample solution $(R_A)$ 105; the double-layer capacitance between electrode A and test sample solution $(C_A)$ 106; the resistance of the test sample solution within the sensor body 100, is termed by $(R_S)$ 107; the resistance of electrode B/solution interface $(R_B)$ 108; and a double-layer capacitance of electrode B/solution interface $(C_B)$ 109. The capacitor array forming the biosensor 110, is interfaced with the capacitive detector circuit 200. The Op Amp buffer 201 increases the input impedance of the detector circuit 110, and ensures a near perfect square wave from the input signal 207. A current signal 208, which is proportional to the amount of hybridization of the analytes with the capture reagents, is detected at the output of circuit 110 due to its impedance. The active amplifier 202, transforms the current signal 208, into a voltage signal 209, whose area under the curve is proportional to the hybridization.

Figure 2:
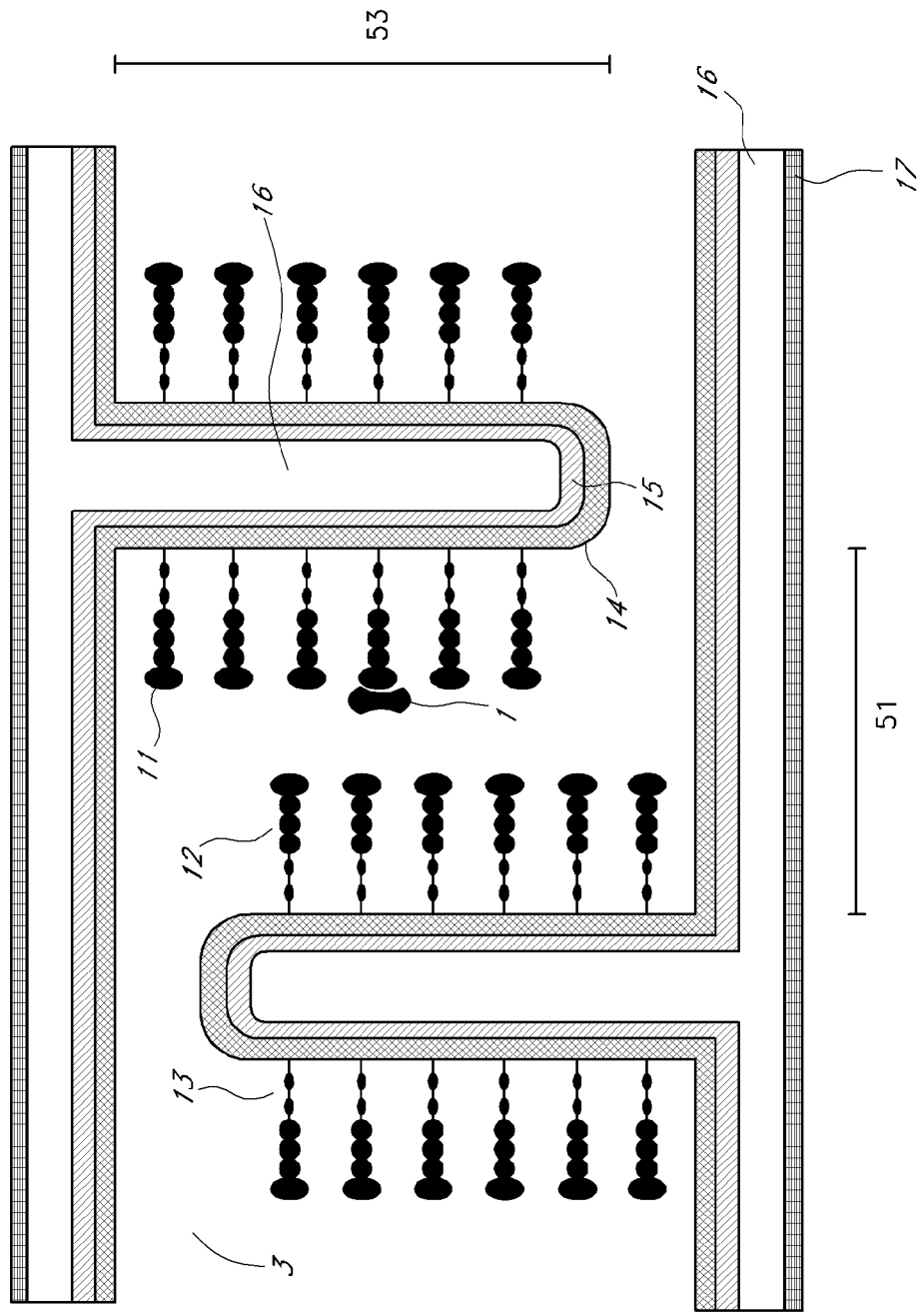
FIG. 2 is a cross section of an isometric view of the capacitive arrangement of the VEGF detector.

FIG. 2 is a cross section of an isometric view of the capacitive arrangement of the VEGF detector. The figure depicts the elements noted by FIGS. 1 & 1A, which further explain and clarify the relationship between the equivalent electronic module 110, and the sensing principles that govern the performance of the VEGF biosensor 100, (inherently depicting the preferred embodiments of this invention). The function of sensor 100, is best defined by the ability of the sensor to effectively immobilize the stranded anti-VEGF aptamers 11, on conducting electrode surfaces 16. The electrolyte solution (medium between the electrodes) is a bodily fluid such as cerebrospinal fluid 3. The electrode 16, is coded with a p-Si substrate 15, to enhance the affinity between VEGF 1, and the anti-VEGF aptamers 11. An insulation layer (silicon dioxide) 14, protects the positively charged substrate 15, which is bonded with a linker (Succinic anhydride) 12, via a hybridization substance (Amino-silanization) 13. The anti-VEGF aptamers (Macugen) are then immobilized by bonding with the linker. The total increase in surface thickness due to the immobilization of the Macugen is about 10 nm. When the VEGF proteins 1, are introduced in the bodily fluid, they bind to the electrode surfaces coded with anti-VEGF aptamers. The binding of the VEGF molecules and anti-VEGF aptamers changes the impedance (mainly its capacitance) of the electrode-solution interface. When the VEGF molecules hybridize with Macugen at its Heparin binding domain, the total thickness is about 200 nm.

The VEGF biosensor is based on an electrochemical approach which exploits a label-free detection technique based on capacitance measurements of bio-modified electrode-solution interfaces. Therefore, the total capacitance of the biosensor 100, can be model as $C_{cell}$ as shown in Equation 2.

$$C_{cell} = C_{geometry} + C_{electrode/solution} \quad (2)$$

$G_{eometry}$ is the capacitance due to the geometry of the sensor as shown in Equation 1. $C_{electrode/solution}$ is double layer capacitance 106, and 109, formed between each of the two electrodes and the solution in the electrochemical cell 110. This double layer capacitance can be modeled as shown in Equation 3. $C_{electrode/solution}$ is represented by $C_A$ and $C_B$ in Equations 9 and 10 for electrodes A and B.

$$\frac{1}{C_{electrode/solution}} = \frac{1}{C_{insulator}} + \frac{1}{C_{linker}} + \frac{1}{C_{Macugen}} + \frac{1}{C_{VEGF}} \quad (3)$$

The total value of $C_{cell}$ is around 10 F/cm² of sensing surface area with a dynamic range of around 3 μF/cm² when all Macugen are bonded with VEGF.

FIG. 2A is a top view of an orthographic representation of the capacitive VEGF sensor, whereby the capacitor plates are identified as to their respective effective geometrical terms $G_x$ 300. The values of A and d are chosen so that the change in capacitance can be effectively measured with the following technique. The boundary conditions for the selection of the dimensions 51 [($d_{cap}$), the distance between the sensor plates in calculating the capacitance value], and 52 [($W_{cap}$), the width of the sensor plates used to calculate the capacitance value] is defined by providing an unrestricted circulation flow of the body fluid through the sensor unit 100, and by setting the hydrostatic flow rate at a constant value, as described in FIG. 2.

Figure 3:
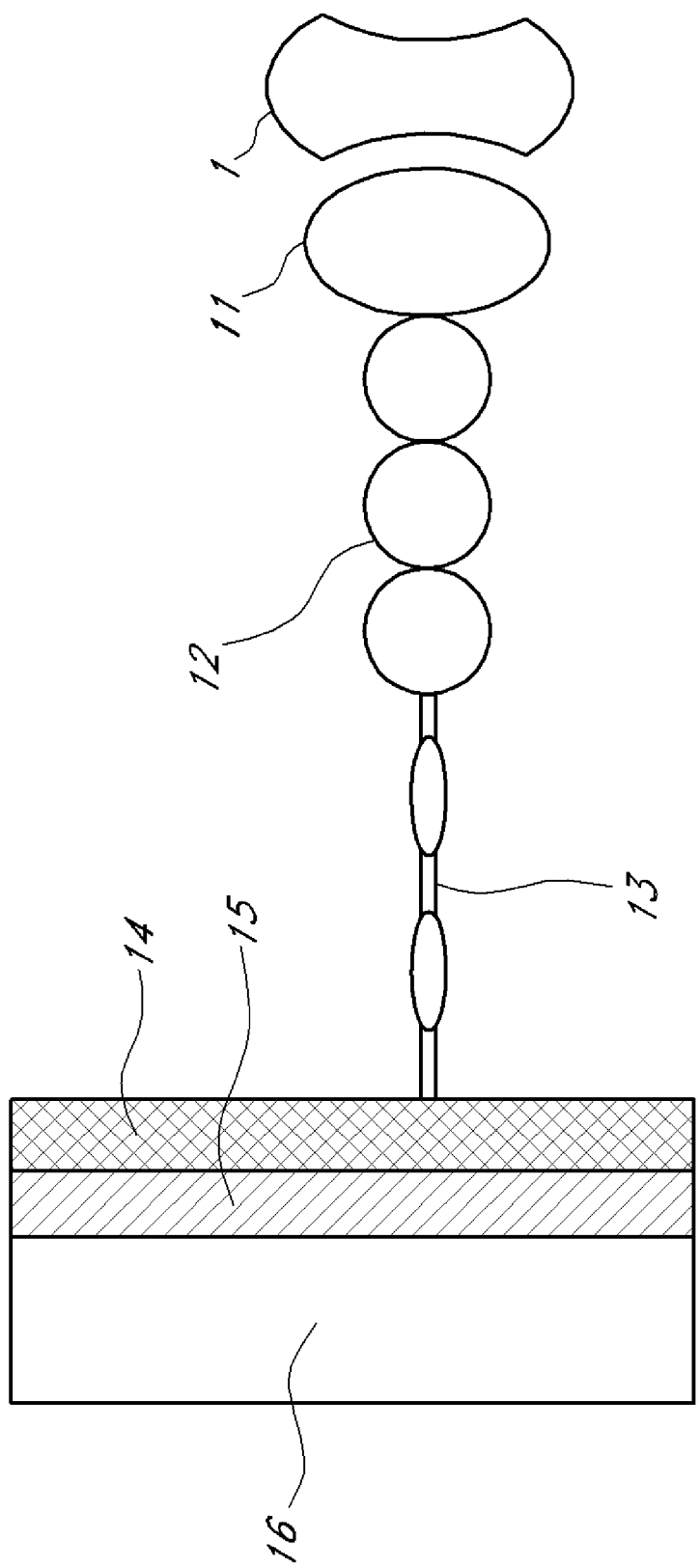
FIG. 3 is a graphic depiction of the VEGF sensor hybridization elements.

FIG. 3 is a graphic depiction of the hybridization between a $VEGF_{165}$ homodimer 1, and the sensor elements. The sensor elements consist of an anti-VEGF aptamer 11, immobilized by its attachment to a linker 12. The linker is Succinic anhydride, also called dihydro-2,5-furandione, an organic compound with the molecular formula $C_4H_4O_3$. The linker 12, is in turn attached to an amino-silanization 13, which binds the entire biological target complex to the insulator surface 14. The positively charged p-substrate 15 under the insulator surface 14 attracts the negatively charged VEGF molecules down to the surface where they bind with the aptamer 11. The conductive electrode 16 provides the interface between the electrochemical cell and the rest of the control system.

Figure 3A:
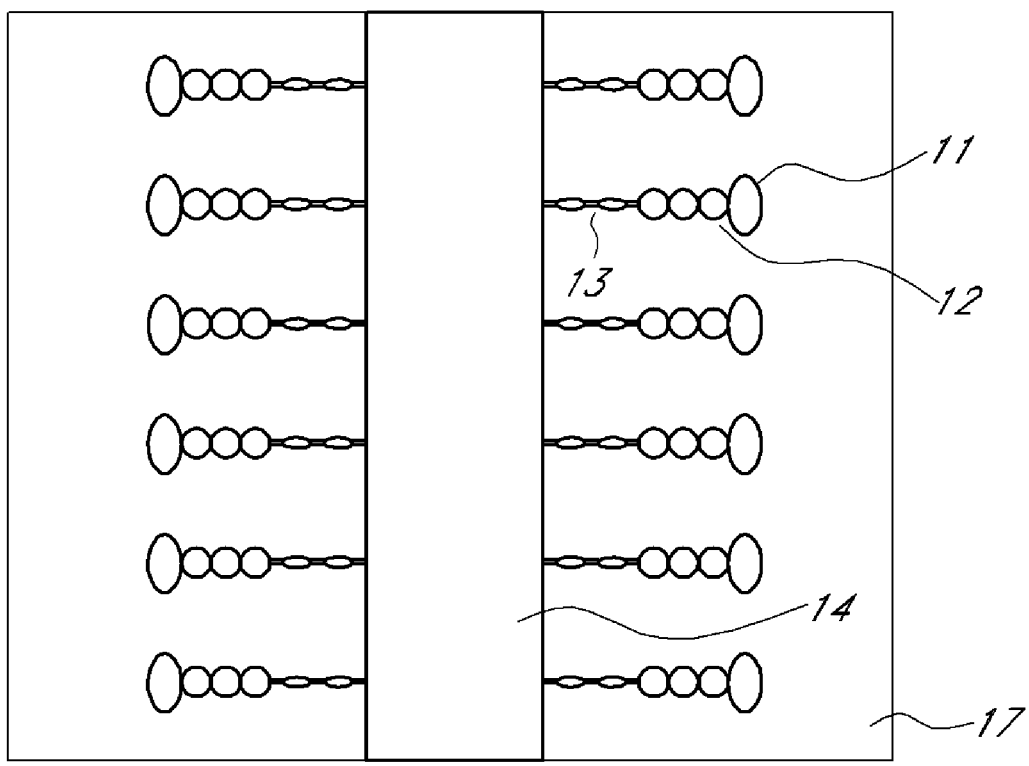
FIG. 3A is a sectional top view of the VEGF detector

FIG. 3A is a sectional top view of the VEGF detector and is provided as one possible configurations of geometry $G_x$ 300, whereby other geometrical layouts are available in forming the biosensor 100.

Figure 3B:
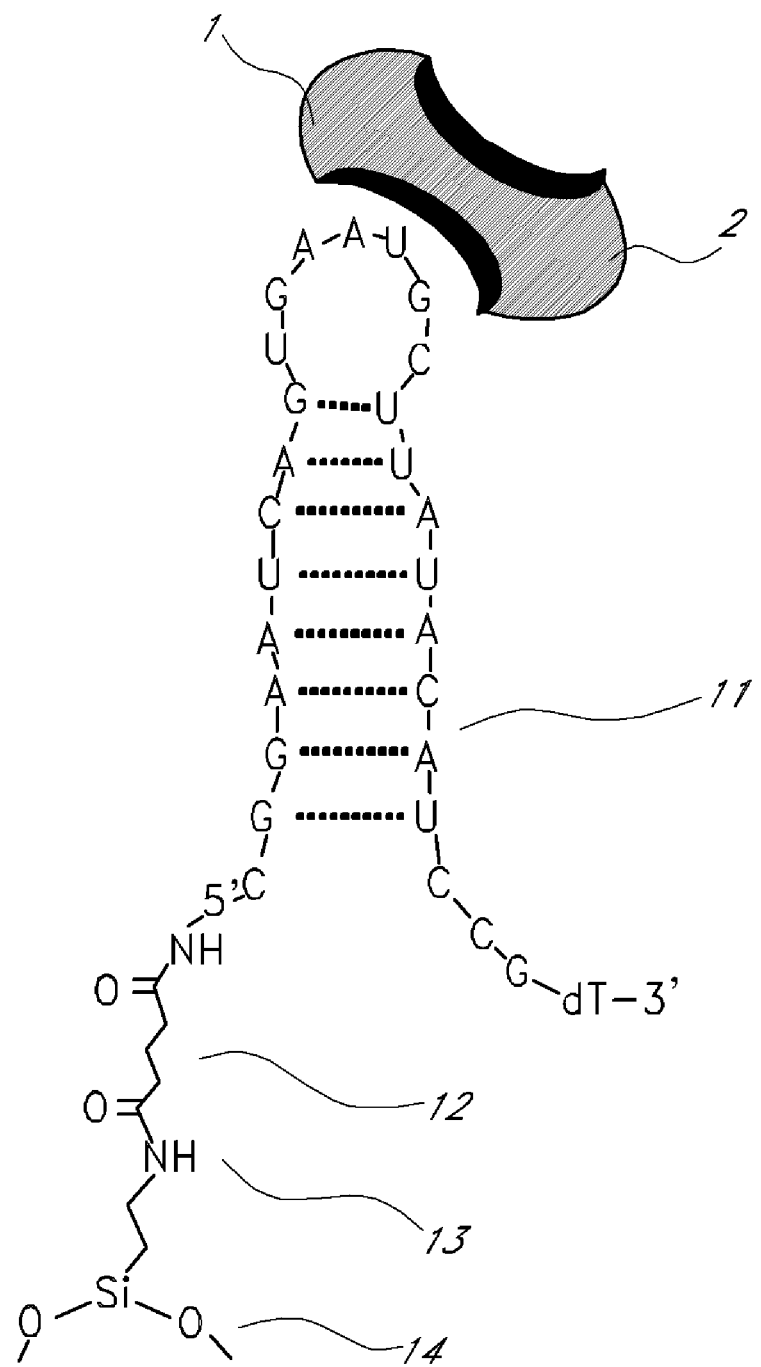
FIG. 3B is a graphic representation of the binding aptamer site with its constituent elements.

FIG. 3B is a graphic representation of the binding aptamer site with its constituent elements. The figure illustrates that $VEGF_{165}$ homodimer 1, which is the most potent and widely expressed isoform and is secreted as a disulfide-linked homodimer with two identical heparin-binding sites, hybridizes with anti-VEGF aptamer (Macugen) 11 at its heparin binding domain 2. A linker 12, such as Succinic anhydride, is useful for producing conjugates of ligands with amine-containing polymers and/or proteins, especially for forming antibody conjugates with chelators, drugs, enzymes, detectable labels and the like. The linker is used as a scaffold between the amino-silanization 13, and the $SiO_2$ insulating surface 14.

Figure 4:
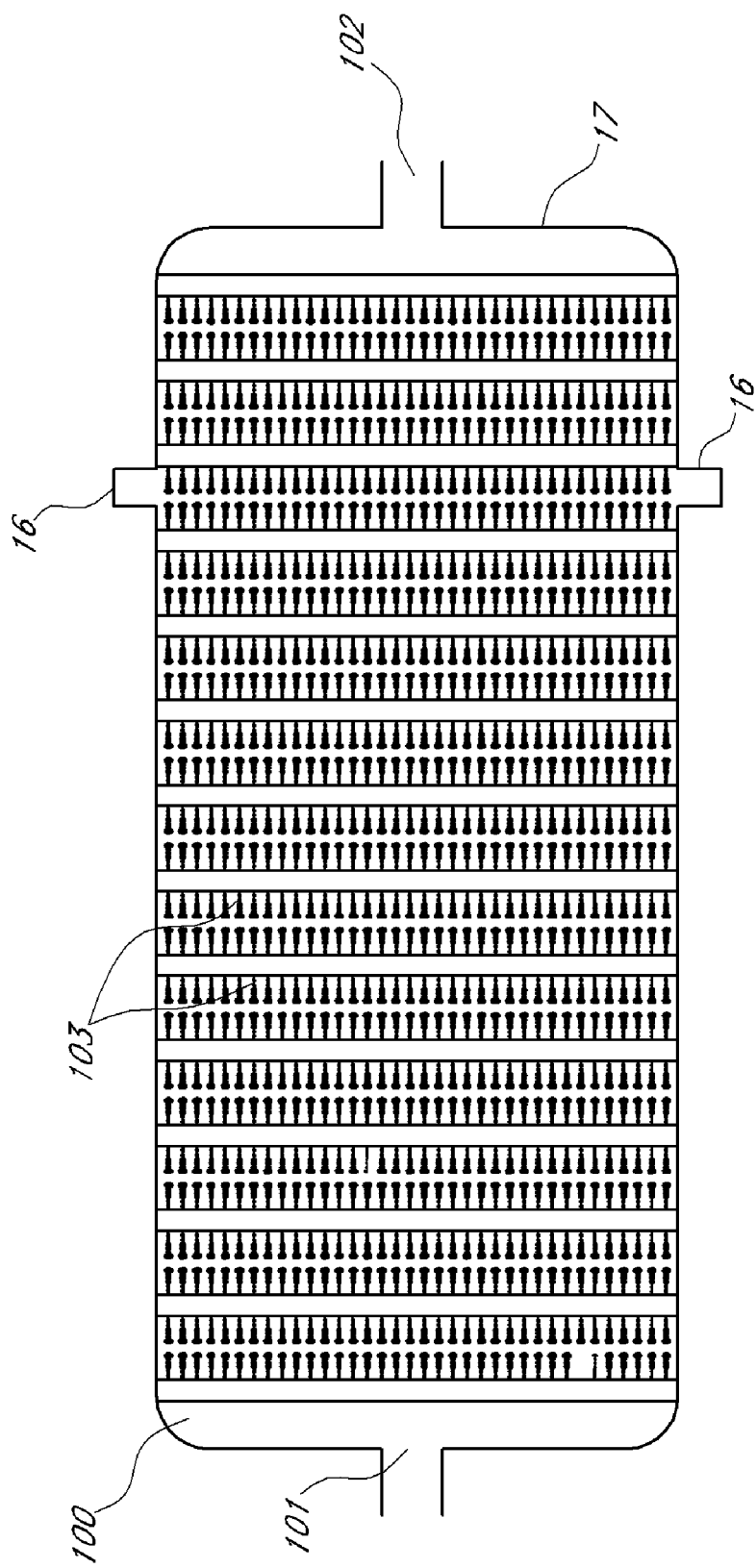
FIG. 4 is a cross sectional view of the biosensor capacitor array with its matrix array layout including the chamber containment.

FIG. 4 is a cross sectional view of the biosensor 100, formed as capacitor with its matrix array 103, layout including the chamber containment 17. The biosensor contains an array of electrodes coded with VEGF sensors forming capacitive plates 103, so as to maximize the response of the capacitive change in the circuit, by providing the largest surface area within the parameter of the biochip enclosure 17. The figure further illustrates the fluid flow inlet 101, and the flow outlet 102, the electrical interface 16, and the insulating enclosure 17 is depicted as the parameters of the proposed device.

Figure 4A:
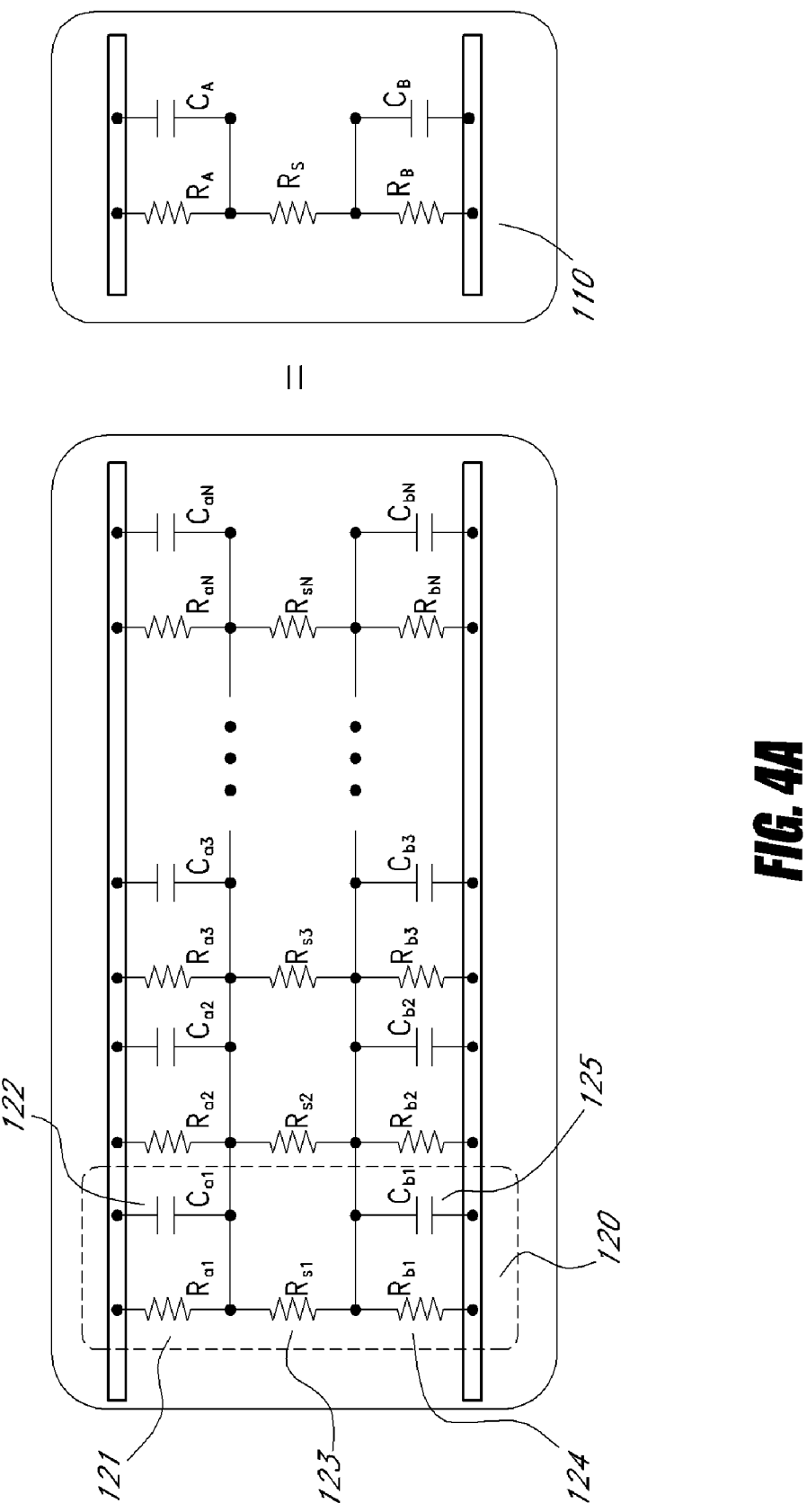
FIG. 4A is a schematic representation of the capacitor matrix array depicting the equivalent circuit.

FIG. 4A shows the equivalent circuit 110 of the VEGF Biosensor 100 and how the circuit can be decomposed to model for each pair of capacitive plates 103 in the capacitor matrix array. Each pair of capacitive plates 103 forms an electrode-electrolyte interface with the solution which can be represented with an equivalent circuit 120. Because the solution medium is dynamic, the circuit for each plate pair is shorted at the electrode/solution interface. Thus, the equivalent circuit of the entire sensor 110 can be written as the combined circuits of each plate pair, which is electrically in parallel to its neighbor pair. Equations 9-13 allow the parameters of 110 be derived from the parameters of each plate pair 120.

$$C_A = C_{a1} \| C_{a2} \| \ldots \| C_{aN} = \sum_N C_{ai} \quad (9)$$

$$C_B = C_{b1} \| C_{b2} \| \ldots \| C_{bN} = \sum_N C_{bi} \quad (10)$$

$$R_A = R_{a1} \| R_{a2} \| \ldots \| R_{aN} = \frac{1}{\sum_N \frac{1}{R_{ai}}} \quad (11)$$

$$R_B = R_{b1} \| R_{b2} \| \ldots \| R_{bN} = \frac{1}{\sum_N \frac{1}{R_{bi}}} \quad (12)$$

$$R_S = R_{s1} \| R_{s2} \| \ldots \| R_{sN} = \frac{1}{\sum_N \frac{1}{R_{ci}}} \quad (13)$$

Figure 5:
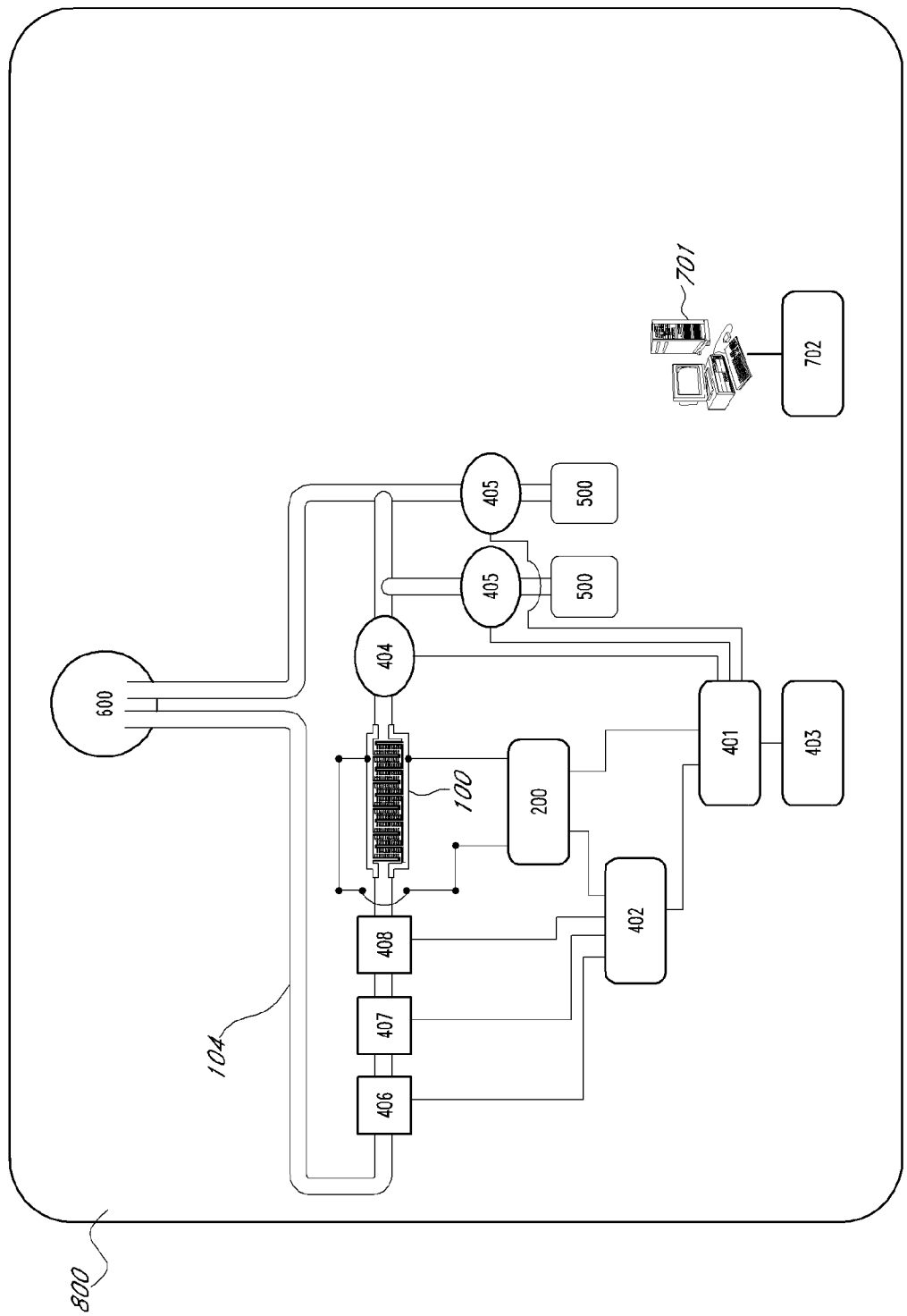
FIG. 5 is a possible layout of the VEGF detector configured within a block diagram of the delivery apparatus.

FIG. 5 is the block diagram of a possible layout of the delivery apparatus 800 including the VEGF Biosensor 100. The diagram shows the VEGF Biosensor 100 in series with other physiological sensors including pressure sensor 406, pH sensor 407, and $SpO_2$ 408 along the catheter tubing 104. A piezoelectric pump 404 circulates the cerebrospinal fluid from the tumor site 600 through the series of sensors. The data from the sensors are acquired by a TI-ADS8344 analog to digital converter 402 for processing by the TI-MSP430 microcontroller 401, which controls the delivery of anti-cancer medications from reservoirs 500 via a set of pumps 405. The MICS transceiver allows the implanted delivery apparatus 800 to be in communication with physician computer 701 via the MICS base station 702.

Figure 5A:
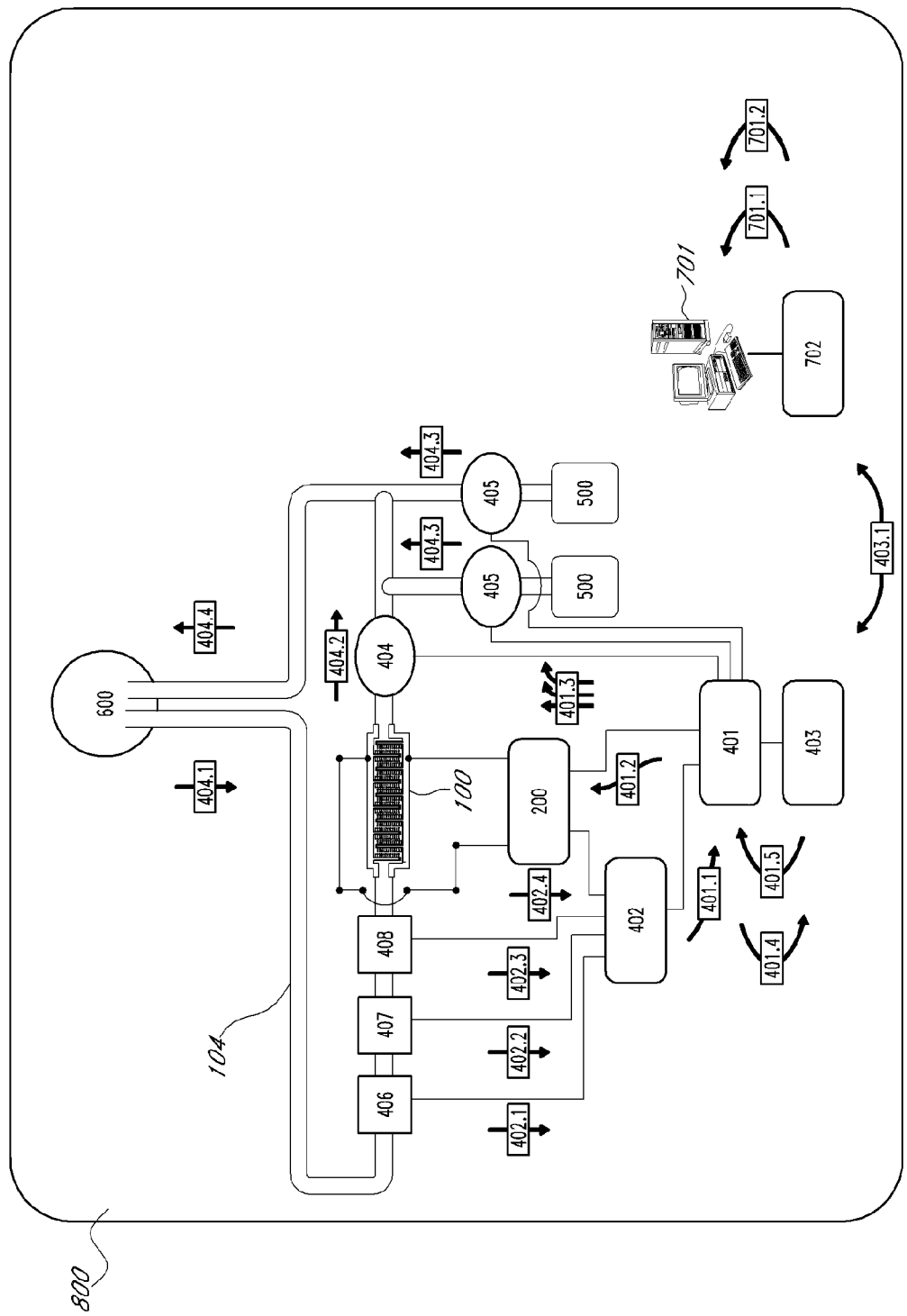
FIG. 5A is a schematic block diagram of the preferred embodiments—biosensor incorporated as part of detecting, analyzing, and reporting system.

FIG. 5A describes the data flow and control mechanism in a possible layout of the delivery apparatus 800. The regulation of the amount of VEGF 1, available for vasculogenesis at the tumor site 600, is accomplished by a circulation pump 404, which controls fluid flow 404.2, bringing test samples from tumor site 404.1, and delivering injected anti-cancer medication 404.4. Additional set of pumps 405 regulates injection of anti-cancer medication 404.3, from reservoirs 500. The test samples brought back from the tumor site are circulated through a series of sensors to acquire information regarding the growth of the tumor and progress of anti-cancer medication treatment. The sensors such as pressure sensor 406, pH sensor 407, $SpO_2$ 408, and VEGF biosensor 100 convert physical and biological information into electrical signals 402.1, 402.2, 402.3, and 402.4. The signals are transformed into data numbers 401.1, by the ADC 402 for processing by microcontroller 401. The microcontroller 401 closes the feedback path for the homeostatic loop (described in FIG. 5B) by sending control signals 401.3, to the pumps 404 and 405, leading to the injection of the anti-cancer medication 404.3. The injection regime is programmed in the "Lookup Tables" or models inside the microcontroller and can be updated 401.5, via a communications link, such as, for example, the Zarlink-70101 medical implant communications services (MICS) transceiver 403. The MICS transceiver can also be used to wirelessly transmit 403.1, sensor data and device status to physician computer 701, for real-time monitoring and data logging 701.1.

Figure 5B:
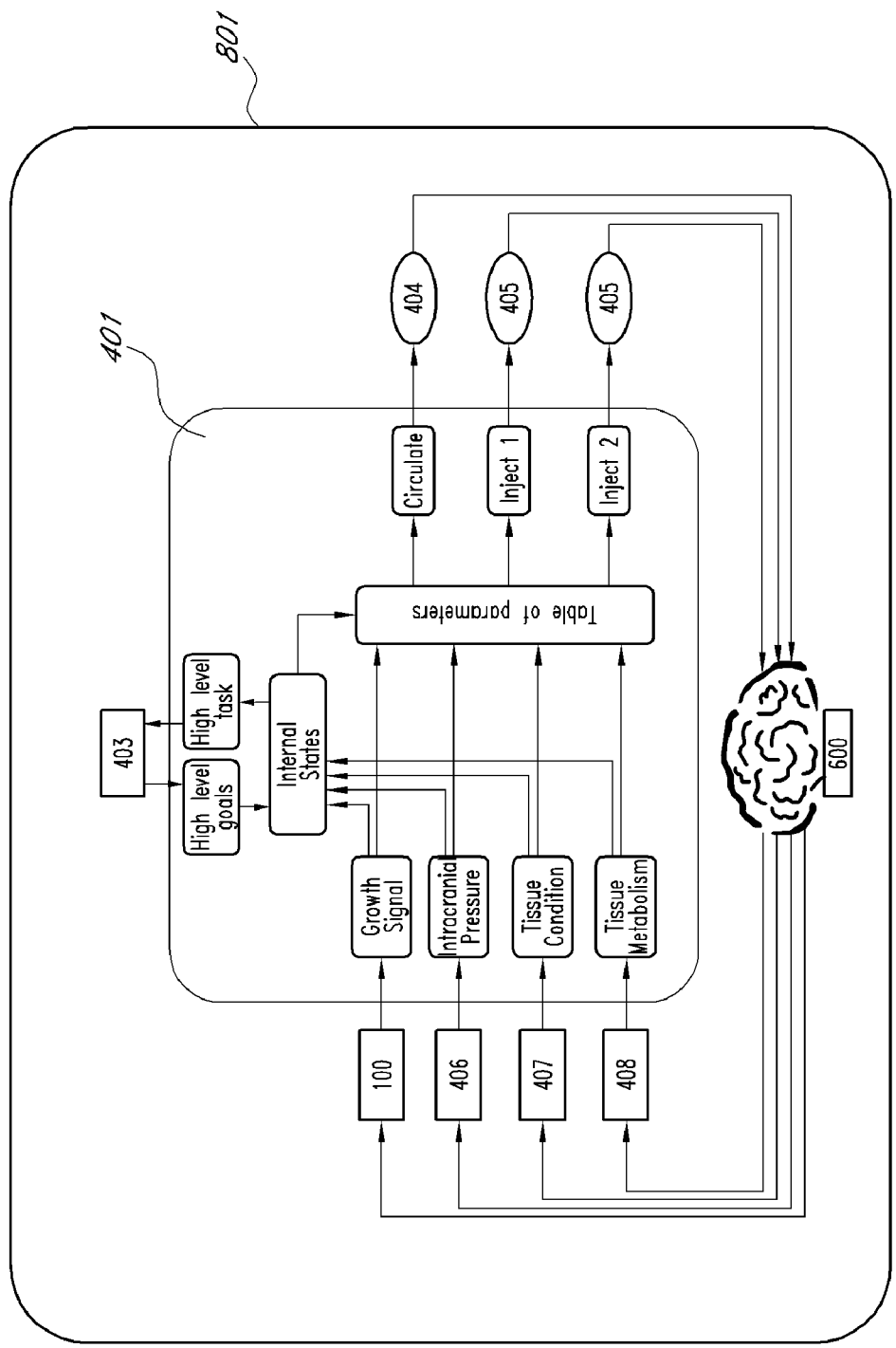
FIG. 5B is a schematic block diagram of the homeostatic loop formed while employing the preferred embodiments of the biosensor.

FIG. 5B is an orthographic representation of the homeostatic loop 801, formed by the embodiments of this invention. The homeostatic approach is used to achieve a stable state of equilibrium that limits the tumor growth while not endangering the surrounding tissues near the tumor site. The homeostatic approach is programmed inside the microcontroller 401 with inputs from sensors such as VEGF biosensor 100, pressure 406, pH 407, and $SpO_2$ 408. Information pertaining to tumor growth such as growth factor, intracranial pressure, tissue condition, and metabolic rate are extracted to determine the progress of treatment based on the parameters in the "lookup table". The sensor information is also used to calculate the internal states which permit adaptation of the system to achieve the desired parameters. The "lookup table" produces actuation parameters to control the pumps that affect the conditions in the tumor site 600. In an embodiment, the lookup table is generated by a physician or caregiver. In an embodiment, the lookup table is generated using empirical data from a cross section of patients. The internal states can be updated based on external inputs from the physician via the wireless transceiver 403.

It is to be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

What is claimed is:

1. An aptamer-probe sensor array for detecting the presence of a target molecule, said sensor array comprising:
    an aptamer which is configured to bind to an indicator protein and change the properties of said indicator protein;
    a probe which is configured to bind to a target molecule, wherein said aptamer and said probe are combined in such a manner that a binding mode between the aptamer and the indicator protein changes when the probe binds to the target molecule;
    a substrate;
    a plurality of sealed micro machined capacitors carried by said substrate, a recognition group including said probe and said aptamer, attached to said capacitor, said recognition group being receptive to the target;
    a detector for sensing each of said plurality of capacitors; and
    a processor configured to compute a result with an indication of the target,
    wherein the recognition group is responsive to VEGF targets.

2. The sensor array of claim 1 wherein at least certain of said capacitors have a plurality of areas, each of said plurality of areas having at least one component of the recognition group including the probe and aptamer attached to said areas.

3. The sensor array of claim 2 wherein certain of said plurality of areas includes at least one component of the recognition group including the probe and aptamer with electrochemical affinity attractive to said target.

4. The sensor array of claim 1 wherein at least one of the plurality of capacitors include a recognition group that bind to the target analyte species; and said sensor with said indicator report said changes to said microcontroller.

5. The sensor array of claim 1 additionally comprising successive layers of first SiO2, Silanization, a Linker such as Succinc anhydride, and a Macugen aptamer acting as an immobilizer, wherein the successive layers cover at least a portion of at least one of the plurality of capacitors.

6. The sensor array of claim 1 additionally comprising analyzing circuitry responsive to said plurality of detectors.

7. A system, comprising:
a sensor including a substrate, a capacitor-array carried by said substrate, a recognition group including a probe and an aptamer attached to said substrate, said recognition group being receptive to a target, and a detector for detecting the target; and
a delivery system for delivering a body fluid for analysis to said sensor,
wherein the recognition group is responsive to VEGF targets.

8. The system of claim 7, wherein said delivery system includes an input port, a reservoir connected to said input port, and an output port connected to said reservoir, at least a portion of said substrate being exposed to the fluid in said reservoir.

9. The system of claim 8, wherein the delivery system includes one or more walls, wherein the walls of said delivery system are of suitable dimensions to provide for an unrestricted circulation flow of the body fluid through the sensor unit.

10. The system of claim 9 wherein the walls of said delivery system are of dimensions defined as a function of a value of a fully charged capacitor, said fully charged capacitor enabling a target binding of maximum functionalized surface area of the sensor array without impairing the circulation flow rate of the body fluid through the sensor unit's walls.

11. A method comprising:
exposing a sensor to a fluid including a target substance, the sensor including a capacitor-array configured to attract the target substance and a recognition group including a probe and an aptamer attached to said capacitor, said recognition group being receptive to the target substance;
analyzing said recognition group to determine if the target substance was found in said fluid; and
modulating a capacitive charge on said capacitors such that the target substance is alternatively attracted and not attracted to said sensor.

12. The method of claim 11, wherein analyzing said recognition group to determine if the target substance was found in said fluid includes direct actuation by an electronic means in contact with said capacitor-array.

13. The method of claim 11, wherein said analyzing includes determining one or more of changes in capacitive value of said biosensor, changes in impedance, and rate of change over time.

14. A system for detecting the presence of a biological molecule, the system comprising:
a fluid flow channel configured to allow at least one fluid including a biological molecule to flow there through;
at least one capacitive element in the fluid flow channel including at least one structure configured to attract the biologic molecule when said capacitive element is charged and to not attract the biological molecule when said capacitive element is not charged; and
a sensor configured to indicate the attraction of the biological molecule.

15. The system of claim 14, wherein the at least one structure is configured to bind to said biological molecule when said capacitive element is charged and to release said biological molecule when said capacitive element is not charged.

16. The system of claim 14, wherein the charging and discharging of the capacitor is modulated so as temporarily attract said biological molecule without causing a buildup said biological molecule sufficient to impede fluid flow.

17. The system of claim 14, wherein the charging and discharging of the capacitor is modulated so as temporarily attract said biological molecule without causing a buildup of said biological molecule and impede the accurate measurement of said biological molecule.

* * * * *